United States Patent [19]
Yao et al.

[11] Patent Number: 5,739,310
[45] Date of Patent: Apr. 14, 1998

[54] RIBOSOMES AS VECTORS FOR RNA

[75] Inventors: Meng-Chao Yao; Rosemary Sweeney; Qichang Fan, all of Seattle, Wash.

[73] Assignee: Fred Hutchinson Cancer Research Center, Seattle, Wash.

[21] Appl. No.: 639,256

[22] Filed: Apr. 23, 1996

[51] Int. Cl.$^6$ .............................. C07H 21/04; C12N 1/00; C12N 15/74; C12N 15/79

[52] U.S. Cl. ............... 536/24.5; 435/172.3; 435/243; 435/320.1; 435/325; 536/24.2

[58] Field of Search .................. 435/320.1, 240.2, 435/325, 172.3, 243; 536/24.5, 24.2

[56] References Cited

U.S. PATENT DOCUMENTS 5,585,479  12/1996  Hoke et al. .............................. 536/24.5

OTHER PUBLICATIONS

Stull et al., "Antigene, Ribozyme and Aptamer Nucleic Acid Drugs: Progress and prospects," *Pharma. Res.*, 12:465–483 (1995).

Sullenger et al., "Expression of Chimeric tRNA–Driven Antisense Transcripts Renders NIH 3T3 Cells Highly Resistant to Moloney Murine Leukemia Virus Replication," *Mol. Cell. Biol.*, 10:6512–6523 (Dec. 1990).

Sweeney R, et al. "Antisense ribosomes: rRNA as a vehicle for antisense RNAs." PNAS 93: 8518–8525, Aug. 1996.

Wakeman JA, et al. "28 S ribosomal RNA in vertebrates." Biochem. J. 258: 49–56, 1989.

*Primary Examiner*—Douglas W. Robinson
*Assistant Examiner*—Amy J. Nelson
*Attorney, Agent, or Firm*—Townsend and Townsend and Crew LLP

[57] ABSTRACT

Methods and compositions are described for the use of ribosomal RNA as a vehicle for heterologous sequences.

20 Claims, 1 Drawing Sheet

RIBOSOMES AS VECTORS FOR RNA

GOVERNMENT SUPPORT

This work was supported by grant MCB-9406322 from the National Science Foundation. The U.S. government may have certain rights in this invention.

BACKGROUND OF THE INVENTION

Ribosomal RNA (rRNA) is characterized by highly conserved regions that represent a core secondary structure. This core secondary structure has been highly conserved in evolution and is believed to be the basic functional unit of the rRNA molecule. These conserved regions alternate with variable regions that differ in length and base composition. The large variations in length that occur between rRNAs of different organisms is generally limited to these variable regions (also known as expansion segments) (for a review, see Michot et al. (*Biochimie* 69:11–23 (1987)). Sweeney et al. (*Mol. Cell. Biol.* 13:4814–4825 (1993) and *EMBO J.* 8: 933–938 (1989)) have shown that insertion of foreign sequences into some sites within the expansion segments in *Tetrahymena* result in functional ribosomes.

Some manipulations of rRNA affect the specificity of ribosomes for mRNA. In a prokaryotic example, Hui et al. (*Proc. Natl. Acad. Sci. U.S.A.* 84:4762–4766 (1987)) disclosed a mutated ribosomal subpopulation directed to a single mutated mRNA species by changing the Shine-Delgarno sequence on the mRNA as well as the anti-Shine-Delgarno sequence on the 16s rRNA into entirely different but complementary sequences.

RNA sequences have been the subject of "antisense" technology in the past. Regulation of gene expression via antisense RNA is a widely used technique for inhibiting expression of a gene of interest. Basically, two different approaches have been taken for the introduction of antisense sequences into a host: transient uptake of extracellular antisense oligonucleotides by the host cell and stable integration of antisense DNA templates in the host cell. Integrated antisense DNA templates (also termed antisense genes) were first demonstrated in eukaryotic cells by Izant and Weintraub (*Cell* 36:1007–1015 (1984)), and subsequently in bacteria by Pestka et al. (*Proc. Natl. Acad. Sci. U.S.A.* 81:7525–7528 (1984)) and Coleman et al. (*Cell* 37:429–436 (1984).

Sullenger et al. (*Mol. Cell. Biol.* 10:6512–6523 (1990) disclosed the introduction of chimeric tRNA genes encoding antisense templates into NIH 3T3 cells via a retrovital vector. They reported that successful use of a tRNA-driven antisense RNA transcription system was dependent on the use of a particular type of retroviral vector, the double-copy (DC) vector, in which the chimeric tRNA gene was inserted in the viral LTR (long terminal repeat). Izant (*Antisense Res. Dev.* 1:371 (1991)) disclosed chimeric snRNP genes consisting of Xenopus U2 small nuclear RNA gene and fragments of the bacterial CAT gene in antisense orientation, chimeric antisense tRNA gene constructed by insertion of CAT gene fragments into a Drosophila tRNA gene and transgenic mouse lines containing antisense U2 and tRNA genes.

The instant invention discloses the use of rDNA sequences, especially expansion segments, as vectors for delivering heterologous RNA to a cell via transcription of the rDNA into rRNA in the cell. These vectors are useful in the therapeutic inhibition of gene expression, including gene therapy, plant engineering and RNA protein binding sites. The enormous copy number, the stability, and the favorable intracellular location of rRNA make it a useful vector for RNA.

SUMMARY OF THE INVENTION

One feature of the invention is a vector comprising a ribosomal DNA sequence having an expansion segment and a heterologous DNA sequence inserted in the expansion segment, wherein the heterologous DNA sequence is capable of being transcribed. The ribosomal DNA sequence can be a large or small subunit RNA gene. The ribosomal DNA sequence can also comprise a tandem repeat of a ribosomal RNA gene. The heterologous DNA sequence can encode, for example, an antisense sequence, a ribozyme, or an RNA binding site for proteins, and may further comprise a sequence encoding a selectable marker.

Another feature of the invention is a method for correlating a nucleotide sequence with a phenotype comprising constructing a library using a vector comprising a ribosomal DNA sequence, wherein a multiplicity of antisense sequences is generated from a host cell genome and each antisense sequence is inserted into an expansion segment of the vector to generate a library. The library is introduced into host cells, and the cells are observed for a desired phenotype. The antisense sequence is used in host cells having the desired phenotype to identify the host cell gene associated with that phenotype.

Another feature of the invention is a host cell containing a vector that comprises a ribosomal DNA sequence having an expansion segment and a heterologous DNA sequence inserted in the expansion segment. The heterologous DNA sequence is operably linked so as to be transcribed, employing suitable promoters, transcription terminators and the like. The ribosomal DNA sequence can be, e.g., a large or small subunit RNA gene, or a tandem repeat of a ribosomal RNA gene.

In another aspect the invention relates to a method for selectively inhibiting the expression of a targeted gene in a host cell. A vector which comprises a ribosomal DNA sequence having an expansion segment and a heterologous DNA sequence inserted in the expansion segment is introduced into the host cell and the heterologous DNA sequence transcribed into RNA. The resulting RNA inhibits the expression of the targeted gene in the host cell.

Figures 1A, 1B:
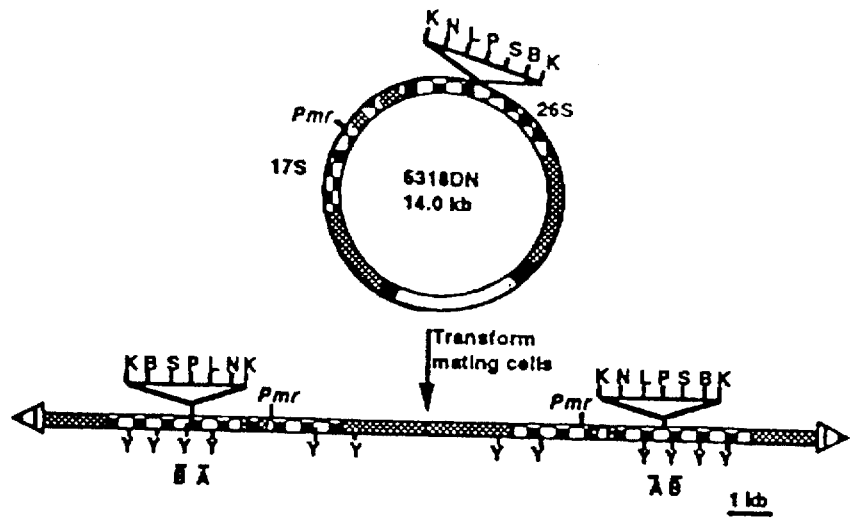
FIG. 1A is a diagram of the vector 5318DN which contains a copy of the micronuclear rDNA including micronuclear-limited flanking sequences (solidly filled); non-coding portions of the rDNA (shaded); coding regions of the rDNA (checkerboard); and pUC19 sequences (unfilled). Capital letters indicate the following restriction sites: K, KpnI; N, NotI; L, SalI; P, ApaI; S, SmaI; B, BstEII; and Y, StyI. Telomeres on the palindromic, macronuclear rDNA are indicated by striped arrowheads. Short lines beneath the diagram show the positions of oligonucleotide sequences A and B used as hybridization probes. Their sequences are as follows.

Oligonucleotide A
5'-TGACAACCCCGTAGTCGGAG-3' [SEQ ID No. 1];
Oligonucleotide B
5'-CGTTTCGCGGACGGGTTTTT-3' [SEQ ID No. 2]; and
Oligonucleotide C
5'CGTTTCGCGGACGGGTTTTT3' [Seq ID No. 3].

"Pmr" indicates the position of a mutation conferring resistance to paromomycin near the 3' end of the 17s rRNA gene that is present on the 5318DN vector.

FIG. 1B is a diagrammatic representation of antisense sequences inserted into the NotI site of 5318DN. The numbers above each diagram denote the position in the sequence of either SerH3 (open box), MLH (shaded box), or α-tubulin (filled box) relative to the initiation codon AUG, with A being +1. Mating *T. thermophila* cells were transformed with the named constructs using an alternate selection protocol for the constructs containing α-tubulin fragments. Growth and immobilization assays were performed as described in Examples herein. Growth rates for αT1A, αT2A and αT3A transformants are from the fast-growing transformed lines described herein. Results of the immobilization assay are indicated as follows: –, not immobilized; +, immobilized; and ND, not determined.

DESCRIPTION OF THE SPECIFIC EMBODIMENTS

The instant invention provides ribosome vectors for delivering heterologous RNA sequences into a host cell. The vectors of the present invention are genetically engineered to contain a heterologous DNA sequence that is transcribed into RNA in the cell. The vectors of the present invention are useful for gene expression in a host cell, including methods for modulating expression of targeted genes in host cells. In some organisms, such as *Tetrahymena*, total replacement of all rRNA genes can be accomplished. However, total replacement of all rRNA genes is not necessary in *Tetrahymena* or other organisms.

In general, ribosomal RNA genes (rDNA) are organized in clusters of tandem repeat units. The tandem repeat units comprise a transcribed portion capable of transcribing both large and small subunits and a nontranscribed spacer (NTS) sequence. In humans, for example, there are between 300 and 400 rRNA genes distributed in five clusters each with an average of 40 repeat units. Human tandem repeats are generally 44 kb of which 13 kb is transcribed into preribosomal RNA (Labella and Schlessinger, *Genomics* 5: 752–760, 1989; which is incorporated herein by reference in its entirety). The preribosomal RNA is subsequently processed into functional ribosomes containing both large and small subunits. For use in the present invention, ribosome vectors may be constructed from a rDNA sequence comprising a tandem repeat unit or a portion thereof. Such repeat units have been cloned and sequenced (see, for example, Neefs et al., *Nuc. Acids Res.* 18(Supp): 2237–2317 (1990); Michot et al., *Biochimie* 69:11–23 (1987); Takaiwa et al., *Nuc. Acids Res.* 12:5441–5448 (1984) and Takaiwa et al., *Gene* 37:255–259 (1984)). Ribosomal RNA genes may be isolated from a wide variety of organisms using standard techniques based on conservation of sequences (see, for example, Hassouna et al., ibid., 1994; Maden et al., *Biochem. J.* 246:519–527 (1987); which are incorporated herein by reference in their entirety). In some embodiments of the invention, it may be preferable to use the entire repeat unit which contains one native expression control regions.

Within one embodiment of the invention, ribosome vectors are constructed comprising the rDNA sequence of a tandem repeat unit wherein a heterologous DNA sequence is inserted into an expansion repeat of the repeat unit. Transformation of cells with linear DNA fragments by calcium phosphate precipitation or microinjection results in the integration of multiple tandem repeats of the fragment into the host genome. Tandem repeat units of rRNA genes characteristically exist as multiple tandem repeats in the genome.

In some embodiments, the use of a smaller portion(s) of the tandem repeat may be preferable. These portions include, but are not limited to the transcription unit capable of transcribing the preribosomal RNA, a portion of the transcriptional unit capable of transcribing the large subunit rRNA, a portion of the transcriptional unit capable of transcribing the small subunit rRNA and a portion of the transcriptional unit comprising at least one expansion segment. In cases where less than the tandem repeat unit is used, it may be preferable to include expression control sequences necessary for expression of the rRNA subunit(s). Such control sequence may include promoter and terminator sequences of the native control regions associated with the tandem repeat and heterologous promoters such as the Pol II or Pol III promoter in combination with a suitable terminator sequence.

In some embodiments of the invention, ribosome vectors comprise an rDNA sequence containing at least one expansion segment into which a heterologous DNA sequence is inserted. Such vectors are introduced into a host cell such that the rDNA sequence is inserted into the host genome by homologous recombination with an rRNA gene resident on the host genome, thereby incorporating the heterologous DNA into the host genome. The ribosomes transcribed from such rRNA genes will carry the heterologous RNA in the cell.

Although the term "gene" as used herein typically refers to a transcriptional unit, it is understood that "gene" can also refer to subparts, regions, or fragments of a transcriptional unit. It may be preferable to introduce a mutation into the repeat unit that confers antibiotic resistance for selection purposes. Mutations that confer resistance to antibiotics that act by binding to ribosomes and result in the interference with normal translation include but are not limited to mutations that confer resistance to paromomycin (Bruns et al., *Proc. Natl. Acad. Sci. USA* 82:2844–2846 (1985)) and mutations that confer resistance to anisomycin (Cundliff, in *The Ribosome: Structure, Function and Evolution*, Hill et al., eds., Ch. 41, Am. Soc. Microbiol., Wash. DC (1990)). Mutations that confer antibiotic resistance may be used to select cells carrying the ribosome vectors. However, such mutations are not required for the practice of the invention. Ribosome vectors may be selected using a number of selection methods such as co-transfection with a selectable marker.

Heterologous sequences may be inserted into the expansion segments or sequences of the ribosomal RNA gene using standard methods such as in vitro mutagenesis, PCR mutagenesis, and restriction enzyme digestion and ligation. The choice of a suitable expansion segment for insertion of the heterologous sequence will be evident to one skilled in the art. Expansion segments, which are present only in eukaryotes, are flanked by conserved regions. There are at least three nomenclature systems used to designate divergent domains/expansion segments/variable regions. The "D" nomenclature system is used by Hassouna et al., *Nuc. Acids Res.* 12:3563–3583 (1984)). The three major nomenclature systems are compared and reviewed by Wakeman and Maden (*Biochem. J.* 258:49–56 (1989)). The expansion segments form extensive hairpin structures and generally increase in size from lower to higher eukaryotes (reviewed by Wakeman and Maden, *Biochem. J.* 258:49–56 (1989)). In general, suitable expansion segments are those that are accessible to the target sequences. Han et al. (*Biochemistry* 33: 9831–9844(1994)), for example, demonstrated that certain ribosomal domains are accessible to chemical attack. Suitable expansion segments include, for example, expansion segments D2, D8 and D12. Suitable sites within expansion segments may be determined by insertion of a heterologous sequence, such as an antisense sequence to a specific marker gene, into the site of choice, transformation of a suitable host cell and determination whether the heterologous sequence is effective in disrupting the expression of the marker gene. Suitable marker genes for use in such methods are genes that encode markers that permit the detection of protein expression and include but are not limited to genes that encode surface markers detectable by interaction with antibodies, reporter genes that are detectable by color development or antibiotic resistance, and genes that encode enzymes with detectable activities. In general, the choice of a suitable marker gene will depend on the particular host cell.

Suitable heterologous sequences for insertion into the ribosome vectors may be up to 1 kb or more, typically less than about 500 nucleotides in length, more preferably less than about 250 nucleotides in length. Heterologous sequences suitable for use in the present invention include, for example, but are not limited to antisense sequences, ribozymes, and RNA binding sites for proteins, as described in more detail herein.

For antisense sequences, suitable antisense sequences are at least 11 nucleotides in length and may include the upstream untranslated and associated coding sequences of the target gene. As will be evident to one skilled in the art, the optimal length of an antisense sequence is dependent on the strength of the interaction between the antisense sequence and their complementary sequence on the mRNA, the temperature and ionic environment in which translation takes place, the base sequence of the antisense sequence, and the presence of secondary and tertiary structure in the mRNA and/or in the antisense sequence. Suitable target sequences for antisense sequences include but are not limited to intron-exon junctions (to prevent proper splicing), regions in which RNA/RNA hybrids will prevent transport of mRNA from the nucleus to the cytoplasm, initiation factor binding sites, ribosome binding sites, and sites that interfere with ribosome progression. The use of antisense sequences and their applications are described generally in, for example, Mol and Van der Krul, eds., *Antisense Nucleic Acids and Proteins Fundamentals and Applications*, New York, N.Y., (1992), which is incorporated by reference herein in its entirety.

A ribozyme refers to an RNA molecule having an enzymatic activity that is able to cleave or splice other separate RNA molecules in a nucleotide base sequence-specific manner. Ribozymes have been reviewed, for example, by Symons (*Ann. Rev. Biochem.* 61:641–671 (1992)). In general, a ribozyme is an RNA molecule that has complementarity in a substrate binding region to a specific RNA target, and also has enzymatic activity that is active to cleave and/or splice RNA in that target, thereby altering the target molecule. Such ribozymes may form a hammerhead motif, but the ribozyme may also be formed in motifs that include hairpin, hepatitis delta virus, group I intron or RNAse P RNA motifs (in association with an RNA guide sequence). Examples of hammerhead motifs are described by Rossi et al. (*AIDS Res. Hum. Retrovir.* 8:183 (1992)), hairpin motifs are described by Hampel et al. (*Biochem.* 28:4929 (1989)) and Hampel et al. (*Nuc. Acids Res.* 18:299 (1990)), the hepatitis delta virus motif is exemplified in Perrotta and Been (*Biochem.* 31:16 (1992)), an RNAseP motif is described in Guerrier-Takada et al. (*Cell* 35:849 (1983)), and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target RNA regions and that it has nucleotide sequences within or surrounding that substrate binding site which impart an RNA cleaving activity to the molecule. The design of trans-acting ribozymes may use the guidance provided, for example, by Haseloff and Gerlach (*Nature* 334: 585–591 (1988)); which is incorporated herein by reference in its entirety), Bertrand et al. (*Nuc. Acids Res.* 22: 293–300, (1994)); which is incorporated herein by reference in its entirety) and Berzal-Herranz et al., *EMBO J.* 12: 2567–2574 (1993)).

In addition to antisense and ribozyme inserts, the vectors of the present invention may be used to carry RNA sequences that serve as binding sites for proteins. In one example, the Rev protein of the HIV-1 virus is known to operate through binding to a specific RNA response element (RRE) in the HIV-1 env gene. Rev is required for the expression of essential vital proteins (Yuyama et al., *Nuc. Acids Res.* 22:5060–5067 (1994)). In one embodiment, the RRE site is inserted into a ribosome vector of the invention such that the RRE target sequence acts as a trap for Rev protein thus inhibiting HIV replication.

The ribosome vectors of the present invention may be introduced into suitable cells as linear fragments or may be introduced on suitable vectors. Representative expression vectors may include both plasmid and/or viral vector sequences. Suitable vectors include retroviral vectors, vaccinia vital vectors, CMV viral vectors, BlueScript™, baculovirus vectors, and the like. Suitable vital vectors include retrovital vectors (see Miller, *Curr. Top. Microbiol. Immunol.* 158: 1–24 (1992); Salmons and Gunzburg, *Human Gene Therapy* 4:129–141 (1993); Miller et al., *Methods in Enzymology* 217: 581–599, (1994)) and adeno-associated vectors (reviewed in Carter, *Curr. Opinion Biotech.* 3:533–539 (1992); Muzcyzka, *Curr. Top. Microbiol. Immunol.* 158:97–129 (1992)). Other vital vectors that may be used within the methods include adenoviral vectors, herpes viral vectors and Sindbis viral vectors, as generally described in, e.g., Jolly, *Cancer Gene Therapy* 1:51–64 (1994); Latchman, *Molec. Biotechnol.* 2: 179–195 (1994); and Johanning et al., *Nucl. Acids Res.* 23:1495–1501 (1995), each incorporated herein by reference). The choice of vector will rely in part on the cell type targeted, the disease state that is being treated and the size of the gene to be transferred.

It may be preferable to use a selectable marker other than a mutation in the rDNA gene which confers resistance to antibiotics to identify cells that contain the cloned rDNA. However, in some embodiments, cells containing the cloned rDNA may be identified by the use of a selectable marker that is introduced with the ribosome vector by co-transfection or by construction of a ribosome vector containing sequences encoding a selectable marker, such as ribosome vectors containing plasmid or viral vector sequences. Selectable markers will generally permit the simultaneous identification and physical separation of cells expressing the marker by, for example, allowing cells expressing the marker to survive while other cells die (or vice versa). Typical selectable markers include but are not limited to resistance to antibiotics and toxins. Selectable markers also include genes that confer resistance to drugs, such as neomycin, hygromycin and methotrexate. Selectable markers may also complement auxotrophies in the host cell. Yet other selectable markers provide detectable signals, such as bioluminescence, peroxidase production, luciferase, beta-galactosidase and blue-green fluorescent protein to identify cells containing the cloned rDNA molecules.

In some embodiments of the invention, selection can be accomplished by subjecting cultured cells harboring and expressing a desired ribosome vector as follows. If the targeted gene encodes a cell surface marker or antigen or other compound associated with the surface of the cell, antibodies specific for that marker (e.g., her-2) that are conjugated to a toxic compound such as ricin can be reacted with the cells in culture. Cells not expressing the ribosome vector will have the targeted gene product expressed on the cell surface, making it available for reaction with the antibody. Such cells are susceptible to killing by the toxic conjugate, whereas cells expressing the antisense construct will not make the gene product and thus will survive. Similarly, a specific antibody can be reacted with cell surface structure, after which the population of cells is passed over an affinity column with specificity for the antibody used. Thus, cells expressing the antisense construct will pass through the column in a much-enriched form. Screening can also be done by observing such aspects of growth as colony size, halo formation, etc. Screening can additionally be accomplished by binding to antibodies, as in an ELISA. In some instances the screening process is preferably automated so as to allow screening of suitable numbers of colonies or cells.

Selectable markers may be amplifiable. Such amplifiable selectable markers may be used to amplify the number of sequences integrated into the host genome. The choice of a suitable selectable marker will be evident to one of ordinary skill in the art and will be guided, for example, by the type of vector used and the host cell type.

Suitable host cells for use in the present invention, include bacterial, fungal, algal, mammalian, arian, insect and plant cells. Within certain embodiments of the invention, the ribosome vectors of the present invention are introduced into tissues from the host organism either in vivo or ex vivo. Manipulations in plants are especially convenient since many plants are totipotent, i.e., a plant can be regenerated from a single cell.

Ribosome vectors of the invention are typically introduced to cells by transformation or transfection of the host cells by a variety of means including electroporation, calcium phosphate precipitation, microinjection and microprojectile bombardment. If the cell type is insusceptible to natural and chemical-induced competence, but susceptible to electropotation, one would usually employ electroporation. If the cell type is insusceptible to electroporation as well, one can employ biolistics. The biolistic PDS-1000 Gene Gun (Biorad, Hercules, Calif.) uses helium pressure to accelerate DNA-coated gold or tungsten microcarriers toward target cells. This process is applicable to a wide range of cells, including plant, bacterial, fungal, algal and animal. It may also be used on animal tissues, tissue culture cells, and animal embryos. One can employ electronic pulse delivery, which is essentially a mild electroporation format for tissues in animals and patients (See, for example, Zhao, *Advanced Drug Delivery Reviews* 17:257–262 (1995)). After introduction of a ribosome vector, the cells are optionally propagated to allow expression of genes to occur.

Cells or tissue samples can be obtained from a host organism and treated ex vivo to introduce the ribosome vector, then returned to the host organism by, for example, injection, implant, and inhalation. Methods for targeting particular cells or tissues of interest in a whole organism may be achieved by a number of methods including viral gene transfer systems, e.g., employing viral capsids, and packaging into liposomes.

Some examples of targets for inhibition by ribosome vectors of the present invention include but are not limited to oncogenes, viruses, genes encoding defective gene products, parasites, and genes encoding metabolic functions or other polypeptides that are candidates for manipulation.

Some examples of target genes in plants include genes regulating pigmentation such as chalone synthase, genes involved in fruit softening such as polygalacturonase, and plant viruses such as cucumber mosaic virus (CMV) and potato virus X (PVX).

Viruses can be RNA or DNA viruses, single or double-stranded, circular or linear. Examples of viral targets include but are not limited to herpes viruses, influenza virus, HIV, Rous sarcoma virus (RSV), vesicular stomatitis virus (VSV), simian virus 40 (SV40), hepatitis B virus, and human papilloma virus (HPV).

Ribosome vectors of the present inventions may be used to treat pathological states (with exemplary target polypeptides) including but limited to restenosis (c-myb, cdc 2 kinase and PCNA and c-myc), leukemia (c-myb, bcr-abl, p53), B cell lymphoma (BCL-2), colon cancer (PKA/RI alpha), malignant melanoma (c-myb, NF-kB/p65, p120), fibrosarcoma (NF-KB/p65), hypertension (angiotensin II type-1), neuronal function (c-fos, kinesin), ischemia (N-methyl-D-aspartate receptor), axonal growth (SNAP-25), neuropsychiatric disorders (D2-dopamine receptor), memory inhibition (ependymin), hepatitis (HBV), genital warts (HPV), and AIDS-related retinitis (CMV).

Examples of nuclear transcription factors as targets include but are not limited to c-myc, N-myc, c-myb, B-myb, c-fog, c-jun, NF-kappa B, Egr-1, c-erbA (R-T3) and other nuclear factors such as pS2, p120, PCNA (cyclin), and cdc2. Examples of growth factors as targets include but are not limited to R-EGF, TGF alpha, R-FGF-1, bFGF (FGF-2), insulin-like growth factors, PDGFA, TGF betas, her-2/neu. Examples of cytokines as targets include but are not limited to CSF-1, c-fms (R-CSF-1) and CSF-1, GM-CSF, G-CSF, M-CSF, R-GM-CSF, erythropoietin, c-kit, c-mpl, TNF alpha, and interleukins including but not limited to IL1 alpha, IL1 beta, r-IL-1, IL4, IL6, IL8, IL11. Examples of protein kinases as targets include but are not limited to PKA alpha subunit, PKC epsilon subunit, PKA type II, pKA type I, caseine kinase, c-src, lck, blk, fyn, lyn, c-fes, c-abl. Examples of membrane or cytoplasmic oncoproteins include but are not limited to G protein, GS alpha, c-Ha-ras, K-ras, and N-ras. Examples of cytosolic serine protein kinases include but are not limited to mos, c-raf-1, or myeloblastine. Additional targets include but are not limited to bcr-abl, bcl2, mdr 1, dhfr, p53, Rb, promthymosine, fibronectin, ICAM t, and rrg.

The ribosome vectors of the invention can also be used to generate transgenic animals by techniques well known in the art (see, for example, U.S. Pat. No. 4,736,866).

Additionally, the ribosome vectors of the invention can be used for genetic analysis of the host organisms by generating null phenotypes for genetic analysis. In this embodiment, a ribosome vector library is made of the host's genome or of random sequence. The library is introduced into a population of cells and screened or selected for desired phenotype. The antisense insert is recovered from the cell or cells having the desired phenotype and is then used, preferably as a hybridization probe or primer in the polymerase chain reaction, to find the gene responsible for or contributing to phenotype. To utilize the information contained in the antisense sequence, the antisense sequence can be cloned out, or simply sequenced by a PCR reaction primed by primers having adjacent sequences from the rDNA vector.

The following examples are offered by way of illustration, not by way of limitation.

EXAMPLES

*Tetrahymena thermophila* is a particularly suitable organism for the study of rRNA genes (rDNA). It is a single-celled eukaryote containing two nuclei: a diploid micronucleus that is transcriptionally silent and a polyploid macronucleus that is actively transcribed. During conjugation the micronucleus undergoes meiosis, nuclear fusion, mitosis and differentiation to produce new micronuclei and new macronuclei. The micronucleus contains one allelic pair of rRNA genes. The rDNA is excised from the chromosome, converted to a 21 kb head to head dimer, and amplified to about 9,000 copies as a new macronucleus differentiates. Mating *T. thermophila* cells can be transformed with a cloned copy of the micronuclear rDNA bearing a mutation conferring paromomycin resistance. This molecule is converted to macronuclear form rDNA as the new macronucleus develops and can completely replace the macronuclear rDNA of the host.

To demonstrate that antisense fragments carried within the rRNA can effectively eliminate expression of a wide range of target genes, portions of three *T. thermophila* genes were inserted into the rDNA vector 5318DN and used to transform *T. thermophila* cells. In the resulting transformants, antisense activity was assessed by determining target protein levels (for two nonessential genes) or viability of transformed lines (for one essential gene). These data indicated that antisense fragments inserted within the rRNA can drastically reduce or eliminate expression of the target genes.

I. Construction of a Ribosome Vector

The pIC19-based ribosome vector, 5318DN, was constructed as described by Sweeney et al., (*Mol. Cell. Biol.* 13:4814 (1993)(FIG. 1A). This vector contains a 61 bp linker [SEQ ID NO:4] with a unique NotI site inserted in the *T. thermophila* LSU rRNA gene D2 variable region. The sequence of the rDNA is provided in Engberg and Nielsen, *Nuc. Acids Res.* 18:6915 (1990). The vector contains a copy of the micronuclear rDNA including micronuclear-limited flanking sequences; non-coding portions of the rDNA; and coding regions of the rDNA. Briefly, a plasmid containing a micronuclear copy of the Tetrahymena rDNA as well as a gene conferring ampicillin resistance was partially digested with DdeI. A plasmid containing the kanamycin resistance gene flanked by polylinkers, including a NotI site, was linearized by digestion with DraI to create a blunt-ended linear fragment. The blunt-ended fragment was ligated to an adapter having one blunt-end, and internal KpnI site and a terminal DdeI adhesive end to obtain a fragment having DdeI adhesive ends flanking polylinkers containing NotI and KpnI sites and the kanamycin resistance gene. The DdeI fragment was ligated with the partially digested rDNA-containing plasmid. Plasmid DNA isolated from kanamycin-resistant, ampicillin-resistant transformants was digested with NotI and religated to remove the kanamycin resistance gene. The positions of the insertions were determined by restriction analysis. One plasmid containing a NotI linker insertion at position 5318 of the rDNA was designated 5318DN. Plasmid 5318DN was constructed such that upon transformation, 5318DN is converted to macronuclear form rDNA having a 21 kb palindrome bearing two copies of the rDNA plus telomeres.

II. Construction of rDNAs Containing Antisense Insertions

Three *T. thermophila* genes, SerH3, MLH, and α-tubulin, were chosen as target genes to demonstrate the ability of ribosome vectors to decrease protein expression. SerH3 is thought to be non-essential for cell growth, while MLH is known to be non-essential for cell growth. The SerH3 gene encodes a surface protein detectable in cells grown between 20° C. and 36° C. Other surface antigen genes are expressed under different growth conditions. Immunologically distinct SerH proteins are found in different wild-type strains. The MLH gene encodes linker histone proteins that are localized specifically in the micronucleus. This gene produces a preprotein which is cleaved to form the β, δ and γ proteins. The α-tubulin gene, which is a single copy gene, is likely to be essential since it has been found to be essential in *Saccharomyces cerevisiae*.

Three fragments, each having sense (S) and antisense (A) counterparts, of each of the target genes were prepared for insertion in the rDNA vector. The SerH3 fragments consisted of one covering the 31 bases between the 5' end of the mRNA and the initiation codon AUG (Ser16A and Ser16S); a second covering this region plus 46 bases of the non-coding region (Ser12A and Ser12S); and a third covering a 31 base region near the middle of the coding region (Ser18A and Ser18S). The MLH gene fragments consisted of one covering the 76 bases between the 5' end of the mRNA and the initiation codon (MLH2A and MLH2S); a second covering the 31 bases immediately upstream of the initiation codon (MLH1A and MLH1S); and a third covering the first 46 bases of the mRNA (MLH3A and MLH3S). The α-tubulin gene fragments consisted of a first fragment corresponding to the 55 bases immediately 5' to the translation start of the α-tubulin gene (αT1A and αT1S) a second fragment corresponding to the first 49 bases of the α-tubulin mRNA from −85 to −37 (where +1 corresponds to the A of the initiation ATG codon) (αT2A and αT2S), and a third fragment corresponding to the 85 bases between the 5' end of the α-tubulin mRNA and the translation start of the α-tubulin gene (αT3A and αT3S).

Fragments were amplified from total *T. thermophila* DNA prepared according to the method of Austerberry and Yao (*Mol. Cell. Biol.* 7:435–443 (1987)) using polymerase chain reaction (PCR) amplification (Ser12, MLH2, MLH3, αT1, αT2 and αT3 constructs). Alternatively, double stranded fragments were obtained by hybridization between single-stranded oligonucleotides (Ser16, Ser18, and MLH1 constructs) and subsequent fill-in with Klenow enzyme as necessary (Ser16). Each fragment was constructed to include flanking NotI adhesive ends to permit insertion into the 5318DN at the unique NotI site. The NotI fragment corresponding to the sequences from −30 to +46 of the *T. thermophila* gene (SER12A and SER12S of FIG. 1B), was amplified from total *T. thermophila* DNA using the primers shown in SEQ ID NOS: 5 and 6. To amplify the DNA, reactions were prepared containing 5 μg of Tetrahymena DNA, 0.1 μg of each primer (SEQ ID NOS: 5 and 6), and MgCl$_2$ at a final concentration of 2 mM. The reactions were covered with paraffin, heated briefly to 65° C. to melt the paraffin and returned to ice to permit the paraffin to resolidify. To the top of the reactions, 2 units of Taq polymerase (GIBCO-BRL, Gaithersburg, Md.), 0.1×volume of 10×BRL reaction buffer and dNTPs at a final concentration of 0.2 mM were added in a total reaction volume of 25 μl. The reactions were amplified over 30 cycles (95° C. for 60 seconds, 51° C. for 80 seconds and 72° C. for 90 seconds). The product was gel purified and digested with NotI prior to ligation to the NotI-linearized 5318DN vector, which had been phosphatased to prevent recircularization. The resulting ligation mixture was transformed into bacterial strain EPICUREAN COLI XLR-Blue MRF' (Stratagene). Plasmid DNA prepared from transformants were analyzed to identify clones containing the insert in both orientations.

The fragment corresponding to −30 to +1 of the Ser3H gene (SER16 of FIG. 1B) flanked by NotI sites was obtained by hybridizing oligonucleotides of SEQ ID NOS: 6 and 7, filling in by Klenow, followed by digestion with NotI. The NotI fragment was inserted into the linearized vector and transformed as described above.

The fragment corresponding to +604 to +634 of the Ser3H coding sequence (Ser18A and Ser18S of FIG. 1B) was obtained as a NotI adapter prepared by hybridizing oligonucleotides of SEQ. ID NOS: 8 and 9. The adapters were phosphorylated to facilitate subcloning. The NotI adapter was inserted into the linearized vector and transformed as descried above except that the ligation was digested with NotI before transformation to reduce transformation of plasmids lacking insert.

The fragments corresponding to αT1 (A and S), αT2 (A and S) and αT3 (A and s) of FIG. 1B were prepared by PCR amplification of total *T. thermophila* DNA under the conditions described above. Fragment αT1 (A and S) was amplified using SEQ ID NOS: 10 and 11. Fragment αT2 (A and S) was amplified using SEQ ID NOS: 11 and 12. The fragments were digested with NotI and gel purified prior to ligation to the NotI-linearized vector. As described above, plasmid DNAs from transformant clones were analyzed to identify clones containing the inserts in both orientations.

The primers used were as follows:

In a second transformation using αT1A, αT2A and αT3A, an alternate selection protocol was used because of the poor transformation using the initial protocol. After transformation, cells were brought to a total volume of 20 ml in 10 mM Tris (pH 7.4) and 100 µl of the cell suspension was plated into each well of a 96-well microtiter plate, in 10 mM Tris (pH 7.4) (100 ml per well). After 12 hours at 30° C., cells were brought to a final concentration of 30 µg/ml paromomycin in suPP. At 48 hours after transformation, 50 µl of suPP plus paromomycin was added, bringing the final concentration to 130 µg/ml.

IV. Target Protein Level Determination

To measure the antisense effect of the antisense rDNA vectors, target protein levels were assayed by Western blot for both genes. For transformants containing the SerH3 series of rDNA vectors, SerH3 gene expression was monitored by a cell immobilization assay (Smith and Doerder, *Genetics* 130:97 (1992), which is incorporated herein by reference in its entirety).

Cell extracts were prepared according to a method modeled on the procedure described by Doerder and Berkowitz (*J. Protozool.* 33:204 (1986)). Transformed lines were grown at 30° C. in supplemented protease peptone media plus paromomycin (130 µg/ml) and control lines were grown in the same medium without the paromomycin. Cells ($10^6$ cells) in mid- to late-log phase were harvested and washed once in cold 10 mM Tris (pH 7.5). Pellets were harvested (Ser12 constructs)
5'-GATGGTACCGCGGCCGCGAAGTTAAGAAATTATTAAGCA-3' [SEQ ID No. 5]
(Ser12 and Ser16 constructs)
5'-GATGGTACCGCGGCCGCTAATTCAAACAAAAAATTCAAAAA-3' [SEQ ID No. 6] (Ser16 constructs)
5'-GATGGTACCGCGGCCGCTTTTTTTTTTTTTGAATTTTTTGTTTG-3' [SEQ ID No. 7] (Ser18 constructs)
5'-GGCCAAGCAAGACAATCAGCAACTGTCCAAGCATT-3' [SEQ ID No. 8]
5'-GGCCAATGCTTGGACAGTTGCTGATTGTCTTGCTT-3' [SEQ ID No. 9]
(αT1 constructs)
5'-CGGATGCGGCCGCACTCTTAAGCAGTCCCTCAAGTA-3' [SEQ ID No. 10]
(αT1 and αT3 constructs)
5'-CGGATGCGGCCGCTTTCTAACTTTTGATTTGGTTTA-3' [SEQ ID No. 11]
(αT3 and αT2 constructs)
5'-CGGATGCGGCCGCTAAAAACAAAAAAAGCAACCTTAAA-3' [SEQ ID No. 12] (αT2 constructs)
5'-CGGATGCGGCCGCTTGAGGGACTGCTTAAGAGT-3' [SEQ ID No. 13].

The structures of all constructs were verified by sequence analysis and the following discrepancies were found: 1) MLH2A contains a 1 bp deletion at position −16 relative to the AUG of MLH; and 2) MLH3S contains two 1 bp deletions, one at position −27 and one at position −49, and a substitution of a T for an A at position −57.

III. Transformation of Mating *T. thermophila* Strains

For each construct mating *T. thermophila* strains CU427 and CU428 (Austerberry and Yao *Mol. Cell. Biol.* 7: 435–443 (1987)) were transformed with 5–10 µg of the named construct by electroporation. Cells were distributed into 96-well plates (100 µl per well) either after resuspension in 20 ml of 10 mm Tris (pH 7.4) or after 5 or 10 fold further dilution into suPP medium (Gorovsky, *J. Cell Biol.* 47:619, 1970). Cells plated in 10 mM Tris were fed after 12–16 hours at 30° C. with one volume of 2×suPP (Gorosky, *J. Cell. Biol.* 47:619–630 (1970)), and eight hours later with 50 µl of suPP medium plus paromomycin to bring the final concentration of paromomycin (Humatin, Parke-Davis, Ann Arbor, Mich.) to 130 µg/ml. After 12 to 16 hours 100 µl of suPP plus paromomycin was added to the cells plated in suPP to achieve a final concentration of 130 µg/ml.

and resuspended in 150 µl of cold 0.1% Triton X-100 in 10 mM Tris (pH 7.5) and vortexed for 20 minutes at 4° to lyse. After lysis, 150 µl of the lysed suspension was added to 2 µl of 0.1N HCl and centrifuged 10 minutes at 19350×g at 4° C. After centrifugation, 113 µl of the supernatant was added to 1.33 µl of 0.1N NaOH plus 56.5 µl of loading buffer (100 mM Tris (pH 6.8), 200 mM dithiothreitol, 4% SDS, 0.2% bromophenol blue, 20% glycerol). The samples were boiled for three minutes. Before loading, 25 mg of urea was mixed with 33 µl of the boiled sample.

For detection of SerH3 gene expression, 25 µl of the urea-sample mixture was loaded onto a 12% SDS polyacrylamide gel (Ausubel et al., in *Current Protocols in Molecular Biology*, John Wiley and Sons, New York, 1990). Western blots were performed using the "ECL" system (Amersham) with minor modifications. The blocking step was performed in the following mixture: 6% casein, 1% polyvinylpyrrolidone, 0.8% NaCl, 75 mM $NaHPO_4$ (pH 7.5) (Gillespie and Hudspeth, *Proc. Natl. Acad. Sci. U.S.A.* 88:2563 (1991). A 1:1000 dilution of the D91 antiserum (Smith et al., *J. Protozool.* 39:420, (1992)) was used as the primary antibody. The secondary antibody was anti-rabbit Ig conjugated to horseradish peroxidase (Amersham) used at a dilution of 1:20,000.

The results of the Western blots demonstrated that SerH3 protein is undetectable in all lines transformed with the two constructs bearing antisense sequences covering the 5' end of the SerH3 mRNA (Ser16A and Ser12A). Thus, these two constructs show complete inhibition of SerH3 expression. However, the third antisense sequence that covers only sequences within the coding region (Ser18A) had no effect. Significantly, all constructs containing SerH3 sequences in the sense orientation had no detectable effect on protein production (Ser12S, Ser16S and Ser18S).

Immobilization assays (Smith, et. al. *Genetics* 130:97–104 (1992)) were carried out at room temperature in a volume of 20 µl at a 1:40 dilution of D91 antisera (Smith et al., supra) and scored after 1 hour. Results of the cell immobilization assay confirmed the results of the Western assay, i.e., all Ser16A and Ser12A transformants failed to be immobilized by an antiserum against the SerH3 protein, while transformants from all other constructs and the control non-transformed cells were immobilized.

For the MLH transformants, protein extracts were prepared according the method described by Guttman et al. (*Cell* 22:299 (1980)) and loaded onto a 15% SDS polyacrylamide gel. The primary antibody used to visualize the MLH proteins was an antibody against the δ protein (Shen et al., *Cell* 82:46 (1995)). The primary antibody was used at a 1:1500 dilution. All MLH2A transformants (which carried an antisense sequence covering the first 76 bases of the mRNA) produced only trace amounts of δ protein (which is encoded by the MLH gene). Transformants from the other two antisense constructs produced normal amounts of δ protein. Again, all three sense constructs had little or no effect on MLH protein production.

V. Analysis of Transformants

To determine whether the antisense fragment insertions disturb rDNA or rRNA function, growth rates of transformed lines as well as their rDNA and rRNA composition were examined.

Total Tetrahymena DNA was prepared for each transformant, digested with StyI, and subjected to Southern blot analysis using oligonucleotide B (FIG. 1A) as a hybridization probe. DNA from untransformed strain CU428 and plasmid constructs (Ser12A, Ser16A, Ser18A, MLH2A and MLH3A) were used as controls. Ser16A, Ser16S, Ser18A and Ser18S transformants contained essentially only rDNA and rRNA with the inserts. Some of these transformed lines contained a small proportion of host rDNA and rRNA. Thus, in all cases, the rDNA is fully, or nearly fully, functional, and the antisense RNA is abundantly present in the cell.

Doubling times of the transformants, determined at 30° C. in suPP plus paromomycin (130 µg/ml), are shown in FIG. 1B. Control cells were shown to have doubling times of between 2.5 to 3.0 hours under similar conditions. As described above, Ser16A, Ser16S, Ser18A and Ser18S transformants contained essentially only rDNA and rRNA with inserts. These transformants grew at rates comparable to wild type lines. These results show unambiguously that the rDNA and rRNA in these lines were fully functional in spite of the insertions. Transformants of Ser12A, Ser12S, MLH2A, MLH2S, MLH3A and MLH3S grew slightly slower than wild type lines. The inserts associated with these transformants may have a slight effect on rRNA function.

VI. Analysis of mRNA Abundance

Northern blot analysis of SerH3 and MLH mRNA levels was carried out to determine whether the antisense rRNAs affected the level of message.

Total Tetrahymena RNA was prepared and subjected to Northern blot analysis. Northern blots were hybridized sequentially with three different probes: oligonucleotide B 5'-CGTTTCGCGGACGGGTTTTT-3'[SEQ ID No. 2] which hybridizes to both transformant type and host type rRNA; a fragment of the MLH gene from nucleotide position 84 to 1785; and a fragment of the SerH3 gene from position 1167 to 1331.

The abundance of SerH3 message was not significantly reduced in any transformed line. In Ser12A and Ser16A transformants (which produced no detectable SerH3 protein), SerH3 mRNA was even more abundant than in untransformed cells, suggesting that some sort of feedback mechanism might be operating at the level of transcription or mRNA stability. The MLH mRNA, however, appeared to be less abundant in most transformed lines, regardless the orientation of the MLE insert. Thus, there was no correlation between mRNA and protein levels. These results indicate that antisense-bearing rRNAs prevent translation of the target genes.

VII. Analysis of α-Tubulin Transformants

An altered selection protocol described above was used to obtain transformants of antisense α-tubulin constructs. Transformants took 2–4 days longer than 5318DN transformants to appear in the initial selection and grew much more slowly. The transformed cells were significantly larger in size and less mobile. Some lines continued to grow very slowly or died (48 out of 160 obtained).

To determine the proportion of the rDNA in putative transformed lines containing an α-tubulin insert, PCR analysis was carried out on the slow-growing or dying cells. Cells selected were either from wells where all remaining cells subsequently died or from wells where the remaining cells continued to grow very slowly (doubling time less than 24 hours). Ten to 20 cells from putative transformants from the microtiter plate in which transformants were selected were transferred to 15 µl of a solution containing 0.5% Tween 20, 0.5% Nonidet P-40, 0.25 mg of proteinase K per ml, and 1×PCR buffer (10 mM Tris-HCl (pH 8.0), 50 mMKCl, 0.005% Tween 20, 0.005% Nonidet P-40, 1.5 mM MgCl 2) as described by Sweeney et al. (*Mol. Cell. Biol.* 14:4203 1994; which is incorporated herein by reference in its entirety). The samples were incubated for 45 minutes at 65° C. and then for five minutes at 95° C. The cell lysate made up no more than 10% of the total volume of the PCR reaction. PCR analysis with primers 5'-TGACAACCCCGTAGTCGGAG-3' [SEQ ID No. 1]
5'-CGTTTCGCGGACGGGTTTTT-3' [SEQ ID No. 2]

indicated that in all cases, a significant proportion of their rDNA contained the α-tubulin insert. This result confirmed that these cell lines were true transformants. Thus, transformation with antisense constructs directed against essential genes can be a lethal event.

Many of the αT1A, αT2A and αT3A transformants remained alive and later began to grow faster with near-normal cell morphology. Southern blot analysis was carried out on some of these lines essentially as described above. Oligonucleotides A and B were used together as hybridization probes. Some of the faster growing lines completely lacked the α-tubulin gene insertion in their rDNA; and the rest contained the insert in only a small proportion (less than or equal to 15%) of their rDNA. The loss of the antisense inserts is likely to be the result of recombination between host and transforming rDNA. Recombination between rDNA molecules in Tetrahymena is known to occur frequently. Recombination could generate molecules in which the insert is lost but the Pmr mutation contained in the 17S RNA gene carried on the transforming rDNA remained thus conferring a selective advantage to the cell. This interpretation was confirmed by the presence of sequences specific to the transforming molecule near the palindromic center of the rDNA in these cells. The data provides further evidence that antisense rRNA directed against the α-tubulin gene inhibited cell growth when present at sufficient copy number. Examination of the rDNA of both dying and healthy transformants lead to the conclusion that antisense α-tubulin rRNA worked effectively against the α-tubulin gene. It also indicated that α-tubulin is an essential gene and that a low proportion of the rDNA bearing the antisense insertion is sufficient to eliminate enough α-tubulin expression to cause lethality. A roughly similar proportion of the rDNA is sufficient to inhibit SerH3 gene expression.

As a control, constructs bearing α-tubulin sequences in the sense orientation (αT1S, αT2S and αT3S) were also analyzed. Although these transformants grew more slowly than normal cells (FIG. 1B), most of them contained the expected insert in the vast majority of their rDNA as determined by Southern analysis. Thus, cell lethality is specific to the antisense sequences.

Thus, these experimental results demonstrate the effective use of rDNA as a vector for antisense sequences. The enormous copy number, the stability, and the favorable intracellular location of rRNA make it a unique and highly attractive vehicle for RNAs with specific biological activities, especially those that act on mRNAs.

All references cited herein are incorporated by reference in their entirety for all purposes.

Although the foregoing invention has been described in some detail by way of illustration and example for purposes of clarity of understanding, it will be obvious that certain changes and modifications may be practiced within the scope of the appended claims.

What is claimed is:

1. A vector comprising a ribosomal DNA sequence having an expansion segment and a heterologous DNA sequence inserted in the expansion segment, wherein the heterologous DNA sequence is transcribed.

2. The vector of claim 1 wherein the ribosomal DNA sequence is a large subunit RNA gene.

3. The vector of claim 1 wherein the ribosomal DNA sequence is a small subunit RNA gene.

4. The vector of claim 1 wherein the ribosomal DNA sequence comprises a tandem repeat of a ribosomal RNA gene.

5. The vector of claim 1 wherein the heterologous DNA sequence encodes an antisense RNA sequence.

6. The vector of claim 1 wherein the heterologous DNA sequence encodes a ribozyme.

7. The vector of claim 1 further comprising a DNA sequence encoding a selectable marker.

8. A cultured host cell comprising the vector of claim 1.

9. The host cell of claim 8, wherein the ribosomal DNA sequence is a large subunit RNA gene.

10. The host cell of claim 8, wherein the ribosomal DNA sequence is a small subunit RNA gene.

11. The host cell of claim 8, wherein the ribosomal DNA sequence comprises a tandem repeat of a ribosomal RNA gene.

12. The host cell of claim 8, wherein the heterologous DNA sequence encodes an antisense RNA sequence.

13. The host cell of claim 8, wherein the heterologous DNA sequence encodes a ribozyme.

14. The host cell of claim 8, wherein the vector further comprises a DNA sequence encoding a selectable marker.

15. A method for selectively inhibiting the expression of a targeted gene in a host cell, comprising introducing into the host cell a vector which comprises a ribosomal DNA sequence having an expansion segment and a heterologous DNA sequence inserted in the expansion segment, whereby the heterologous DNA sequence is transcribed into RNA that inhibits expression of the targeted gene in the host cell.

16. The method of claim 15, wherein the ribosomal DNA sequence is a large subunit RNA gene.

17. The method of claim 15, wherein the ribosomal DNA sequence is a small subunit RNA gene.

18. The method of claim 15, wherein the heterologous DNA sequence encodes an antisense RNA sequence specific for a transcription product of the targeted gene in the host cell.

19. The method of claim 15, wherein the heterologous DNA sequence encodes a ribozyme specific for a transcription product of the targeted gene in the host cell.

20. The method of claim 15, wherein the vector is packaged in a viral capsid or liposome.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: rRNA ( x i ) SEQUENCE DESCRIPTION: SEQ ID NO:1:

TGACAACCCC GTAGTCGGAG                        20

( 2 ) INFORMATION FOR SEQ ID NO:2:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: rRNA ( x i ) SEQUENCE DESCRIPTION: SEQ ID NO:2:

CGTTTCGCGG ACGGGTTTTT                        20

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: rRNA ( x i ) SEQUENCE DESCRIPTION: SEQ ID NO:3:

CGTTTCGCGG ACGGGTTTTT                        20

( 2 ) INFORMATION FOR SEQ ID NO:4:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: rRNA ( x i ) SEQUENCE DESCRIPTION: SEQ ID NO:4:

GGTACCCCCA AAGCGGCCGC GTCGACGGGC CCCCCGGGGT AACCTTTGCG GGTACCCTGA    60

G    61

( 2 ) INFORMATION FOR SEQ ID NO:5:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: rRNA ( x i ) SEQUENCE DESCRIPTION: SEQ ID NO:5:

GATGGTACCG CGGCCGCGAA GTTAAGAAAT TATTAAGCA    39

( 2 ) INFORMATION FOR SEQ ID NO:6:

( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( i i ) MOLECULE TYPE: rRNA ( x i ) SEQUENCE DESCRIPTION: SEQ ID NO:6:

GATGGTACCG CGGCCGCTAA TTCAAACAAA AAATTCAAAA AA    42

( 2 ) INFORMATION FOR SEQ ID NO:7:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: rRNA ( x i ) SEQUENCE DESCRIPTION: SEQ ID NO:7:

GATGGTACCG CGGCCGCTTT TTTTTTTTG AATTTTTTGT TTG    43

( 2 ) INFORMATION FOR SEQ ID NO:8:

( i ) SEQUENCE CHARACTERISTICS:
            ( A ) LENGTH: 35 base pairs
            ( B ) TYPE: nucleic acid
            ( C ) STRANDEDNESS: single
            ( D ) TOPOLOGY: linear ( i i ) MOLECULE TYPE: rRNA ( x i ) SEQUENCE DESCRIPTION: SEQ ID NO:8:

GGCCAAGCAA GACAATCAGC AACTGTCCAA GCATT    35

( 2 ) INFORMATION FOR SEQ ID NO:9:

( i ) SEQUENCE CHARACTERISTICS:
            ( A ) LENGTH: 35 base pairs
            ( B ) TYPE: nucleic acid

```
        ( C ) STRANDEDNESS: single
        ( D ) TOPOLOGY: linear ( i i ) MOLECULE TYPE: rRNA ( x i ) SEQUENCE DESCRIPTION: SEQ ID NO:9:

GGCCAATGCT TGGACAGTTG CTGATTGTCT TGCTT                                     35

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: rRNA ( x i ) SEQUENCE DESCRIPTION: SEQ ID NO:10:

CGGATGCGGC CGCACTCTTA AGCAGTCCCT CAAGTA                                    36

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: rRNA ( x i ) SEQUENCE DESCRIPTION: SEQ ID NO:11:

CGGATGCGGC CGCTTTCTAA CTTTTGATTT GGTTTA                                    36

( 2 ) INFORMATION FOR SEQ ID NO:12:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( x i ) SEQUENCE DESCRIPTION: SEQ ID NO:12:

CGGATGCGGC CGCTAAAAAC AAAAAAGCA ACCTTAAA                                   38

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: rRNA ( x i ) SEQUENCE DESCRIPTION: SEQ ID NO:13:

CGGATGCGGC CGCTTGAGGG ACTGCTTAAG AGT                                       33
```